United States Patent [19]
Quentin

[11] Patent Number: 5,932,817
[45] Date of Patent: Aug. 3, 1999

[54] FLASK SEALING SYSTEM AND MICROWAVE TREATMENT APPARATUS WITH SUCH A SEALING SYSTEM

[75] Inventor: Eric Quentin, Briare, France

[73] Assignee: Societe Prolabo, Fontenay-Sous-Bois, France

[21] Appl. No.: 08/765,870

[22] PCT Filed: May 9, 1996

[86] PCT No.: PCT/FR96/00698

§ 371 Date: Mar. 19, 1997

§ 102(e) Date: Mar. 19, 1997

[87] PCT Pub. No.: WO96/35937

PCT Pub. Date: Nov. 14, 1996

[30]  Foreign Application Priority Data

May 11, 1995 [FR] France ................................. 95 05594

[51] Int. Cl.[6] ...................................................... G01N 1/00
[52] U.S. Cl. ........................ 73/863.11; 220/240; 219/756
[58] Field of Search .................................. 219/679, 687, 219/688, 704, 707, 756, 734, 772, 385, 428; 220/203.01, 203.08, 240, 315, 323, 324, 326; 73/863.11

[56]  References Cited

U.S. PATENT DOCUMENTS

| | | | |
|---|---|---|---|
| 2,299,401 | 10/1942 | Melton ..................................... | 219/428 |
| 3,635,370 | 1/1972 | Romanavskas .......................... | 220/315 |
| 5,095,886 | 3/1992 | Schmed ................................... | 220/240 |
| 5,369,034 | 11/1994 | Hargett et al. .......................... | 219/687 |
| 5,407,641 | 4/1995 | Katschnig et al. ...................... | 219/679 |
| 5,427,741 | 6/1995 | Bennett ................................... | 219/756 |
| 5,496,110 | 3/1996 | Geier et al. ........................ | 220/203.01 |
| 5,542,576 | 8/1996 | Arment ................................... | 220/323 |

*Primary Examiner*—Robert Raevis
*Attorney, Agent, or Firm*—Jacobson, Price, Holman & Stern, PLLC

[57]  ABSTRACT

A sealing system for sealing one or more flasks (10) with a longitudinal X–X' axis, open at a first end thereof (11) for introducing a sample and positioned inside microwave apllication cavity (100) for heating the sample is described. The system of the invention comprises a cap (20) to be partially inserted in the flaask along the X–X' axis so as to close the open end thereof and retaining meaans (30) for holding the cap in a flask sealing position, wherein the portion (22) of said cap which is inserted in the flask has a peripheral skirt (23) capable of sealingly engaging the inner wall (12) of the flask under an excess pressure created therein by heating the sample with microwaves.

13 Claims, 2 Drawing Sheets

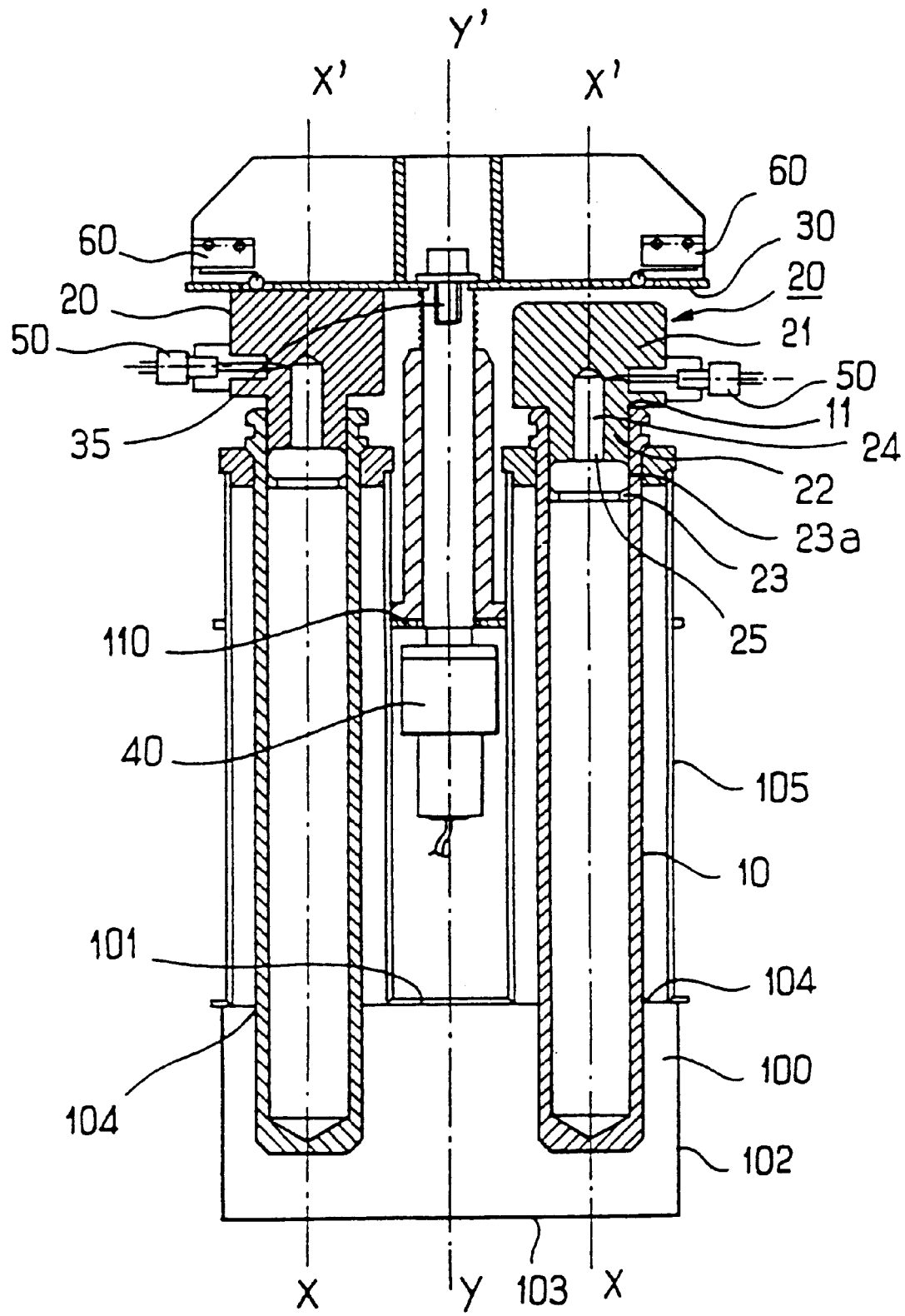
FIG_1

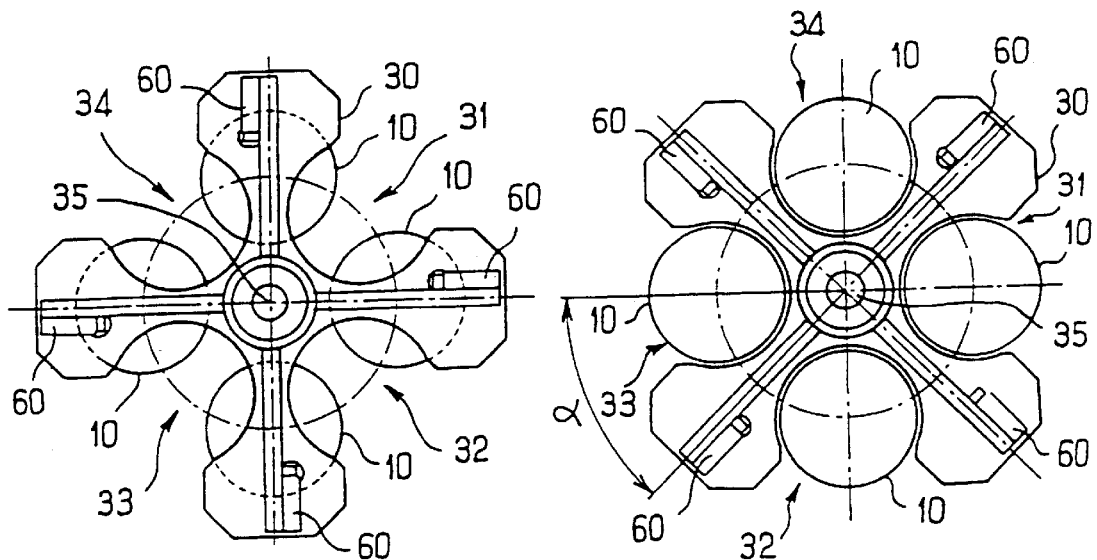
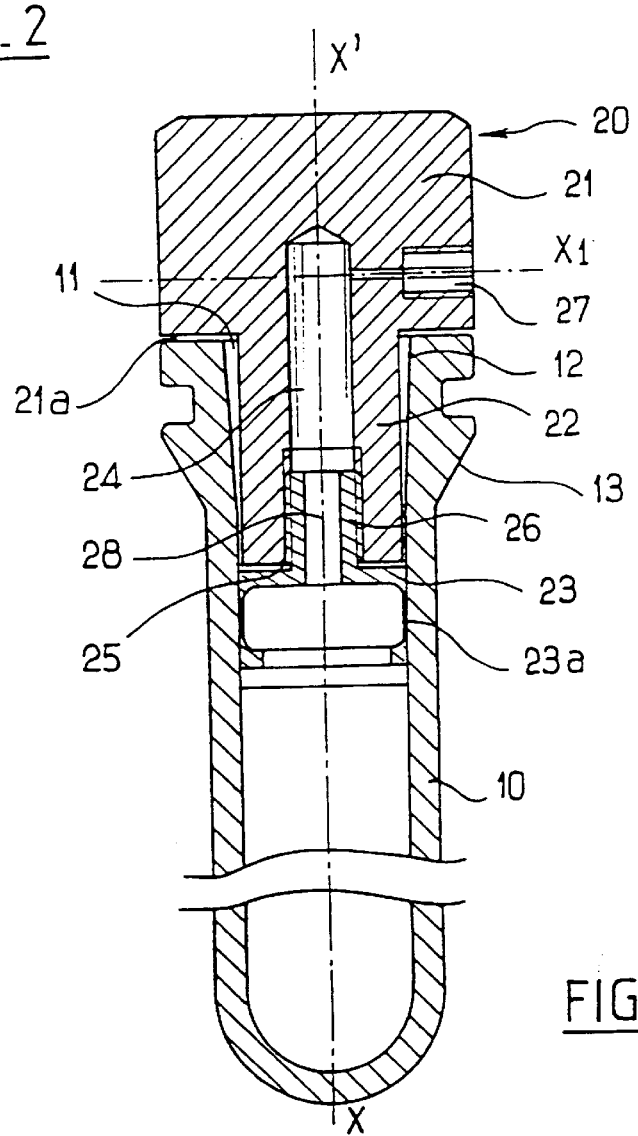

FLASK SEALING SYSTEM AND MICROWAVE TREATMENT APPARATUS WITH SUCH A SEALING SYSTEM

The present invention relates to a system for sealing at least one flask of longitudinal axis X–X' which is open at a first end for the introduction of a sample and which is positioned inside a microwave-application cavity with a view to heating the sample.

The invention also relates to apparatus for carrying out a treatment in a wet environment on a number of samples at the same time, the apparatus employing microwave heating of the samples and including such a sealing system.

Such apparatus finds a particularly advantageous use in carrying out chemical reactions such as mineralization, saponification, hydrolysis, speciation, and organic synthesis, for example.

Another particularly advantageous use of the apparatus according to the invention is the extraction under the effect of microwaves in a solvent of organic or inorganic compounds dispersed in soils, sediments, waters, plants, biological products or alternatively polymers.

In particular the invention relates to an improvement to the apparatus described in French patent applications nos 93 157 35 and FR 2 681 431 belonging to the Applicant Company, this apparatus including means for emitting microwaves into a microwave-application cavity of cylindrical shape operating in the open condition.

Already known apparatus of this type which operates in the closed condition, under pressure, generally comprises a microwave-application cavity in which bombs closed by screw-on caps are arranged.

This type of apparatus does, however, have several drawbacks.

This is because the bombs cannot contain large volumes of sample because the greater the volume of the sample, the more gas is given off under pressure when the sample is heated, which does not allow the bomb to work.

Furthermore, such apparatus working with bombs comprising screw-closure devices can work only in one condition, that is to say in the condition closed under pressure. It is not possible first of all to carry out degassing by making the apparatus work in the open condition then to close said apparatus to work under pressure.

The invention proposes a new sealing system which is fitted on a flask in a simple way allowing the flask to work in the open condition or closed condition, this making it possible to treat large volumes of samples by first of all carrying out an initial degassing operation before closing the flask.

More particularly, according to the invention, the sealing system includes:

a stopper intended to be pushed partially into said flask along the axis X–X' so as to seal its open end, retaining means capable of holding said stopper in a position for sealing said associated flask, that part of the stopper which is engaged in said flask including a peripheral skirt which can be pressed in leaktight fashion against the internal wall of the flask under the effect of an overpressure which there is in this flask once the sample has been heated by microwaves.

According to a preferred embodiment of the invention, the means of retaining the sealing system comprise a bearing surface which can be positioned at right angles to the axis X–X' above each stopper, the relative position of the bearing surface and of the stopper allowing the latter to slide inside the flask along the axis X–X' in the direction of the bearing surface so as to come to bear against the latter under the thrusting force induced by the overpressure which there is inside the flask upon heating of the sample.

Furthermore, advantageously, in the sealing system in accordance with the invention, the skirt of each stopper is fitted with a lip capable of pressing in leaktight manner against the internal wall of the associated microwave-heated flask under the effect of the internal overpressure.

In accordance with the preferred embodiment of the invention, it includes a pressure sensor connected to the bearing surface and capable of recording the overpressure which there is inside said flask through the bearing surface bearing on the stopper.

Furthermore, according to this preferred embodiment, the bearing surface of the sealing system in accordance with the invention carries at least one detector capable of coming into contact with each stopper bearing against said bearing surface and of emitting a signal which signals the presence of a stopper against said bearing surface.

According to a particularly advantageous feature of the sealing system in accordance with the invention, the bearing surface is mounted so that it can rotate about an axis Y–Y' parallel to the axis X–X' on a support secured to the application cavity between, on the one hand, an open position in which it is positioned offset from each flask giving unimpeded access to the open end of said flask for the fitting or the removal of the associated stopper or alternatively to allow said flask to be heated in the open condition, and, on the other hand, a closed position in which it is positioned above each flask fitted with the associated stopper, sealing its opening.

According to another embodiment of the sealing system in accordance with the invention, it includes a number of stoppers, each of said stoppers being intended to be pushed into a flask of axis X–X', said stoppers being capable of coming to bear against said bearing surface positioned at right angles to the axis X–X' above said stoppers under the thrusting force induced by the overpressure which there is inside said flasks upon microwave heating of the samples.

The description which will follow with reference to the appended drawing, which is given by way of non-limiting example, will make it easy to understand the essence of the invention and how it may be realized.

In the appended drawings:

FIG. 1 represents a diagrammatic view in longitudinal section of microwave-treatment apparatus including a sealing system in accordance with the invention, FIG. 2 is a view from above of the apparatus of FIG. 1, the sealing system being in a closed position above the flasks, FIG. 3 is a diagrammatic view from above of the apparatus of FIG. 1, the sealing system being in an open position, FIG. 4 is a diagrammatic detail view of the stopper of the sealing system in accordance with the invention, the stopper being positioned inside a flask.

Represented in FIG. 1 is apparatus for carrying out a treatment in a wet environment on a number of samples which is contained in a number of flasks, here four flasks, the apparatus employing microwave heating of the samples.

Such apparatus is described structurally and functionally in its entirety in French patent applications FR 2 680 431 and no. 93 157 35 belonging to the Applicant Company. Consequently the apparatus as a whole will not be re-described here and the present description relates in detail only to the system for sealing such apparatus which corresponds to a specific embodiment thereof.

The application cavity 100 represented here is cylindrical of revolution of central axis of symmetry Y–Y' and includes an upper wall 101, a side wall 102 and a lower wall 103. The side wall 102 of the application cavity 100 includes a window, not represented here, which is transparent to microwaves and via which a waveguide (also not represented) emerges inside said cavity. This waveguide is connected to a microwave generator, not represented, and conveys the microwaves as far as the application cavity. The upper wall 101 of the application cavity 100 here includes four circular openings 104, only two of which are represented, these being arranged in twos symmetrically opposed with respect to the axis Y–Y'. Moreover, the application cavity 100 on the outside on its upper wall 101 carries four identical cylindrical wells 105, two of which are represented here. Each cylindrical well 105 extends toward the outside of the cavity, at right angles to the upper wall 101, starting from each circular opening 104 provided in said upper wall 101. The section of each well 105 corresponds to the section of each opening 104 and the height of each well is such that it forms a microwave absorption barrier to avoid microwaves being propagated to the outside of the application cavity. The vertical axes X–X' of the cylindrical wells 105 are parallel to the axis Y–Y' and pass through the centers of the openings 104.

The samples to be treated, not represented here, are placed in four flasks 10, just two of which are represented in FIG. 1. Each flask 10 is introduced vertically into each well 105 toward the application cavity 100, via the openings 104 in such a way that part of the flask containing the sample lies in said cavity. When the flasks are positioned in the wells, the axes X–X' of the wells correspond to the axes X–X' of said flasks.

The flasks are made, for example, of quartz or of polytetrafluoroethylene.

Each flask 10 has an open upper end 11 positioned outside each well 105 and allowing the sample to be introduced into the flask 10. As may be seen in greater detail in FIG. 4, the outer surface 13 of each flask 10, near its opening 11, has a conical shape flared upward, which bears on the edge of the opening of each well 105. Thus the edge of the opening of each well 105 forms a support for each flask positioned inside the application cavity 100.

Furthermore, the apparatus represented in FIG. 1 includes a sealing system which comprises, for each flask 10, a stopper 20 intended to be pushed partly into said flask along the axis X–X' so as to seal its open end 11, and retaining means capable of retaining each stopper 20 in a position for sealing the associated flask. These retaining means consist of a closure lid comprising a bearing surface 30 capable of being positioned at right angles to the axis X–X' above each stopper 20.

As can better be seen in FIG. 4, each stopper 20 includes a head 21 which is cylindrical of revolution about the axis X–X' and protrudes outside each flask 10 when said stopper is partially pushed into the flask, and a body 22 extending substantially at right angles to said head 21 along the axis X–X', engaged with sliding along said axis X–X' in the flask 10. The body 22 includes here at its free end 25 positioned inside the flask, a peripheral skirt 23 capable of pressing in leaktight fashion against the internal wall 12 of the associated flask under the effect of an overpressure which there is in this flask once a sample has been heated by microwaves. More specifically, this skirt 23 includes an annular lip 23a which preferably presses against the internal wall 12 of the flask 10 under the effect of the internal overpressure. It will be observed that the skirt 23 fitted with its lip 23a is cylindrical of revolution about the axis X–X', and is capable of interacting with a portion of the internal wall 12 of the flask which has an upwardly flared conical shape close to its opening 11. This conical shape of the internal wall 12 of the flask advantageously allows the stopper 20 to be removed easily from the flask when the heating of the sample is over.

As can be seen in FIGS. 1 and 4, each stopper 20 includes an axial duct 24 provided in the body 22 of each stopper which extends along the entire length of said body 22 as far as into the head 21. This axial duct 24 which has symmetry of revolution about the axis X–X' is open at the free end 25 of the body 22 and is extended along the axis X–X' by the skirt 23 at this free end 25. The axial duct 24 is connected, close to its other closed end situated in the head 21 of the stopper 20, to a safety device 50 (represented diagrammatically in FIG. 1). The safety device 50 and the axial duct 24 are connected together by means of a duct 27 of axis $X_1$ at right angles to the axis X–X' so that the safety device 50 is subjected to the overpressure which there is inside said flask through said axial duct 24 via the duct 27 of axis $X_1$. This safety device is capable of emitting a signal for shutting down the microwave heating above a given overpressure. The safety device 50 includes a blowout diaphragm, not represented here, positioned in such a way as to close off said duct 27 of axis $X_1$. This blowout diaphragm has the ability, for example, to withstand a pressure of approximately 40 bar, above which pressure it blows and sets off the emission of the shut-down signal.

It should be noted that according to the embodiment represented in FIG. 4, the stopper 20 consists of two parts. A first part of the stopper 20 comprises the head 21 and the body 22 provided with the axial duct 24, and a second part is formed by the peripheral skirt 23 which is extended at the top by a sleeve 26 intended to be fitted in the axial duct 24 along the axis X–X' in order to join the two parts together. Once assembled, the axis 28 of the sleeve 26 of the second part of the stopper is coincident with the axis X–X' of the axial duct 24. Of course it is possible to envisage for the stopper 20 to be made as a single piece.

It should be emphasized that when there is no overpressure inside the flask 10, then the lower surface 21a of the head 21 rests on the peripheral rim surrounding the opening 11 of the flask.

The sealing system in accordance with the invention and represented in FIGS. 1 to 3, includes, as has already been explained, a lid including a bearing surface 30. This lid is mounted so that it can rotate between a closed position and an open position (see FIGS. 2 and 3) by means of a shaft 35, about the axis Y–Y' of the application cavity, this axis Y–Y' being parallel to the axis X–X' of the flasks 10, on a support 110 secured to the application cavity 100 and which extends transversely between the wells. This shaft 35 extends along the axis Y–Y' between the bearing surface 30 positioned at right angles above the stoppers 20 and a pressure sensor 40 positioned below the support 110 along the axis Y–Y'. The bearing surface 30 is mechanically connected to the pressure sensor 40.

As can be seen more particularly in FIG. 1, when there is no pressure inside said flasks 10, the surface of the bearing surface 30 is positioned, when the lid is closed (see FIG. 2) a certain distance away from the stoppers 20. The relative position of the bearing surface 30 and of the stoppers 20 allows the stoppers to slide inside the flasks along the axis X–X' in the direction of the bearing surface 30 so that they come to bear against the latter (see FIG. 1) under the thrusting force induced by the overpressure which there is inside the flasks 10 upon heating of the samples. In this position in which each stopper 20 is bearing, the peripheral skirt 23 equipped with its lip 23a presses in leaktight manner against the internal wall 12 of the associated flask. It will be noted that for this the thrusting force induced by the overpressure which there is in each of said flasks is greater than the gripping force of the peripheral skirt 23 against the internal wall 12 of each flask so that it is possible to open the flask by positioning the lid in the open position (see FIG. 3) once heating is over.

As can also be seen in FIG. 1, the bearing surface 30 carries detectors 60 which are capable of coming into contact with the stoppers 20 bearing against said bearing surface 30 and intended to emit a signal which signals the presence of each stopper 20 against the bearing surface 30. Thus advantageously it is possible to check that each flask is closed using these detectors, checking the presence of the stopper 20 bearing against the bearing surface 30.

As may be seen more particularly in FIGS. 2 and 3, the lid and the bearing surface 30 have a special shape including cells 31, 32, 33, 34 of essentially circular shape. According to the embodiment represented, the bearing surface 30 has four cells. Each of the circular cells has a diameter slightly larger than the diameter of a flask 10. The cells 31, 32, 33, 34 are positioned in twos symmetrically with respect to the axis Y–Y'.

When the lid is in the open position (represented more particularly in FIG. 3), each flask 10 is positioned in each cell 31, 32, 33, 34 of the bearing surface 30 in such a way that said bearing surface 30 is positioned offset from each of the flasks 10. Thus there is unimpeded access to the upper opening 11 of each flask 10 for the fitting or removal of a stopper 20 or alternatively to allow the microwave apparatus and associated flasks to operate open. The latter case may be envisaged for initial degassing of the flasks at the beginning of heating.

When the lid is in the closed position (see FIG. 2), the bearing surface 30 is positioned in a position offset by an angle α from the open position of the lid. In this closed position, the bearing surface 30 is placed above each stopper 20 pushed into each flask 10. Thus as the pressure inside the flasks 10 rises, each stopper 20 comes to bear against said bearing surface 30 and provides a seal at the opening 11 of each flask 10.

As has already been explained, the bearing surface 30 is connected under the support 110 to a pressure sensor 40. This pressure sensor 40 is capable of recording the overpressure which there is in all of the four flasks through the bearing surface bearing on the stoppers 20. This pressure sensor works in tension. This is because the stoppers 20 bearing on the bearing surface 30 exert on the bearing surface 30 an upward tensile force which leads to the compression of a liquid or of calibrated crystals contained within the pressure sensor which allows the sum of the pressures in the flasks to be measured. It is thus possible to evaluate a mean value of the pressure in said flasks. Such a sensor is set to approximately 10 to 15 bar. This sensor advantageously makes it possible to check and control the pressure inside the flasks 10 and may allow automatic control of the apparatus on the basis of the pressure measured.

The present invention is not in any way limited to the embodiment described and represented but those skilled in the art will be able to envisage any alternative forms which conform to its spirit.

Indeed, it is possible to envisage apparatus comprising a greater number of flasks (6, 8 or 10 flasks) comprising a sealing system according to the invention.

I claim:

1. System for sealing at least one flask (10) of longitudinal axis X–X', which is open at a first end (11) intended to allow the introduction of a sample and which is positioned inside a microwave-application cavity (100) with a view to heating the sample, characterized in that it includes:

a stopper (20), intended to be pushed partially into said flask (10), which is movable along the axis X–X' so as to seal the open end (11), retaining means, having bearing surface (30), which is mounted securely on a support (110) forming an integral part of the application cavity (100) in order to hold said stopper (20) in a position for sealing the associated flask (10), the retaining means comprising a bearing surface (30) which can be positioned at right angles to the axis X–X' above each stopper (20), the relative position of the bearing surface (30) and of the stopper (20) allowing the latter to slide inside said flask (10) along the axis X–X' in the direction of said bearing surface (30) so as to come to bear against the latter under the thrusting force induced by the overpressure which there is inside said flask (10) upon heating of the sample, part (22) of the stopper (20) which is engaged in said flask (10) including a peripheral skirt (23) which can be pressed in leaktight fashion against the internal wall (12) of the flask (10) under the effect of an overpressure which there is in the flask once the sample has been heated by microwave.

2. Sealing system according to claim 1, characterized in that the peripheral skirt (23) of each stopper (20) has an external wall which is cylindrical of revolution about the axis X–X' and capable of pressing against said substantially conical internal wall (12) of said flask (10).

3. Sealing system according to claim 2, characterized in that it includes a pressure sensor (40) connected to the bearing surface (30) and capable of recording the overpressure which there is inside said flask (10) through said bearing surface (30) bearing on said stopper (20).

4. Sealing system according to claim 2, characterized in that the bearing surface (30) carries at least one detector (60) capable of coming into contact with each stopper (20) bearing against said bearing surface (30) and of emitting a signal which signals the presence of said stopper (20) against said bearing surface (30).

5. Sealing system according to claim 2, characterized in that the bearing surface (30) is mounted so that it can rotate about an axis Y–Y' parallel to the axis X–X' on said support (110) secured to the application cavity (100) between, on the one hand, an open position in which it is positioned offset from each flask (10) giving unimpeded access to the open end of said flask (10) for the fitting or the removal of the associated stopper (20) or alternatively to allow said flask (10) to be heated in the open condition, and, on the other hand, a closed position in which it is positioned above each flask (10) fitted with the associated stopper (20), sealing its opening (11).

6. Sealing system according to claim 2, characterized in that it includes a number of stoppers (20), each of said stoppers (20) being intended to be pushed into a flask (10) of axis (X–X'), said stoppers (20) being capable of coming to bear against said bearing surface (30) positioned at right angles to the axis X–X' above said stoppers (10) under the thrusting force induced by the overpressure which there is inside said flasks (10) upon microwave heating of the samples.

7. Sealing system according to claim 1, characterized in that the peripheral skirt (23) of each stopper (20) is fitted with a lip (23a) capable of pressing in leaktight manner against the internal wall (12) of the associated microwave-heated flask (10) under the effect of the internal overpressure.

8. Sealing system according to claim 1, characterized in that each stopper (20) has a head (21) which protrudes outside each flask (10) and a body (22) which extends substantially at right angles to said head (21), engaged with sliding along the axis X–X' inside said flask (10) and being provided with an axial duct (24) which is open at the free end (25) of said body (22), said skirt (23) being positioned level with said free end (25) in the axial extension of said duct (24).

9. Sealing system according to claim 8, characterized in that the axial duct (24) extends from the free end (25) of said body (22), through the entire length of said body (22), and into said head (21) to where it is connected to a safety device (50) intended to be subjected to the overpressure which there is inside said flask (10) by means of said axial duct (24) and capable of emitting a signal for shutting down the microwave heating above a given overpressure.

10. Apparatus for carrying out a treatment in a wet environment on a number of samples which are contained in a number of flasks (10) of axis X–X', the apparatus comprising means for emitting microwaves into an application cavity (100) of central axis of symmetry Y–Y', the application cavity (100) in its upper wall (101) including openings for the introduction of the flasks (10) inside the application cavity (100) parallel to the axis Y–Y', these being arranged in twos so that they are symmetrically opposed with respect to the axis Y–Y', characterized in that it includes a sealing system according to claim 1.

11. System for sealing at least one flask (10) of longitudinal axis X–X', which is open at a first end (11) intended to allow the introduction of a sample and which is positioned inside a microwave-application cavity (100) with a view to heating the sample, characterized in that it includes:

a stopper (20), intended to be pushed partially into said flask (10) along the axis X–X' so as to seal its open end (11), retaining means, having bearing surface (30), which is mounted securely on a support (110) forming an integral part of the application cavity (100) in order to hold said stopper (20) in a position for sealing the associated flask (10), part (22) of the stopper (20) which is engaged in said flask (10) including a peripheral skirt (23) which can be pressed in leaktight fashion against the internal wall (12) of the flask (10) under the effect of an overpressure which there is in this flask once the sample has been heated by microwaves, characterized in that each stopper (20) has a head (21) which protrudes outside each flask (10) and a body (22) which extends substantially at right angles to said head (21), engaged with sliding along the axis X–X' inside said flask (10) and being provided with an axial duct (24) which is open at the free end (25) of said body (22), said skirt (23) being positioned level with said free end (25) in the axial extension of said duct (24), and characterized in that the axial duct (24) extends from the free end (25) of said body (22), through the entire length of said body (22), and into said head (21) to where it is connected to a safety device (50) intended to be subjected to the overpressure which there is inside said flask (10) by means of said axial duct (24) and capable of emitting a signal for shutting down the microwave heating above a given overpressure.

12. Apparatus for carrying out a treatment in a wet environment on a number of samples which are contained in a number of flasks (10) of axis X–X', the apparatus comprising means for emitting microwaves into an application cavity (100) in its upper wall (101) including openings for the introduction of the flasks (10) inside the application cavity (100) parallel to the axis Y–Y', these being arranged in twos so that they are symmetrically opposed with respect to the axis Y–Y', characterized in that it includes a system for sealing said flasks (10) of longitudinal axis X–X', which is open at a first end (11) intended to allow the introduction of a sample and which is positioned inside a microwave-application cavity (100) with a view to heating the sample, characterized in that it includes:

a number of stoppers (20) intended to be pushed partially into said flasks (10) along the axis X–X' so as to seal its open end (11), retaining means, having bearing surface (30), which is mounted securely on a support (110) forming an integral part of the application cavity (100) in order to hold said stoppers (20) in a position for sealing the associated flasks (10), part (22) of each stopper (20) which is engaged in each flask (10) including a peripheral skirt (23) which can be pressed in leaktight fashion against the internal wall (12) of each flask (10) under the effect of an overpressure which there is in each flask once the sample has been heated by microwaves.

13. Apparatus for carrying out a treatment in a wet environment on a number of samples which are contained in a number of flasks (10) of axis X–X', the apparatus comprising means for emitting microwaves into an application cavity (100) in its upper wall (101) including openings for the introduction of the flasks (10) inside the application cavity (100) parallel to the axis Y–Y', these being arranged in twos so that they are symmetrically opposed with respect to the axis Y–Y', characterized in that it includes a system for sealing said flasks (10) of longitudinal axis X–X', which is open at a first end (11) intended to allow the introduction of a sample and which is positioned inside a microwave-application cavity (100) with a view to heating the sample, characterized in that it includes:

a number of stoppers (20) intended to be pushed partially into said flasks (10) along the axis X–X' so as to seal it open end (11), retaining means, which is mounted securely on a support (110) forming an integral part of the application cavity (100) in order to hold said stoppers (20) in a position for sealing the associated flasks (10), the retaining means comprising a bearing surface (30) which can be positioned at right angles to the axis X–X' above the stoppers (20), the relative position of the bearing surface and of the stoppers allowing the latter to slide inside the flasks (10) along the axis X–X' in the direction of the bearing surface so as to come to bear against the latter under the thrusting force, part (22) of each stopper (20) which is engaged in each flask (10) including a peripheral skirt (23) which can be pressed in leaktight fashion against the internal wall (12) of each flask (10) under the effect of an overpressure which there is in each flask once the sample has been heated by microwaves induced by the overpressure which there is inside said flasks (10) upon heating of the sample.

* * * * *